United States Patent [19]

Feldman et al.

[11] 4,393,311

[45] Jul. 12, 1983

[54] METHOD AND APPARATUS FOR SURFACE CHARACTERIZATION AND PROCESS CONTROL UTILIZING RADIATION FROM DESORBED PARTICLES

[75] Inventors: Leonard C. Feldman, Berkeley Heights; Joseph S. Kraus, Stirling; Norman H. Tolk, Mendham; Morton M. Traum, Warren; John C. Tully, Berkeley Heights, all of N.J.

[73] Assignee: Bell Telephone Laboratories, Incorporated, Murray Hill, N.J.

[21] Appl. No.: 380,702

[22] Filed: May 21, 1982

Related U.S. Application Data

[63] Continuation of Ser. No. 159,167, Jun. 13, 1980.

[51] Int. Cl.³ ............... G01N 23/22; H01J 37/26
[52] U.S. Cl. ................... 250/459.1; 250/310
[58] Field of Search ........... 250/307, 310, 365, 423 R, 250/423 P, 425, 427, 461.1, 461.2, 486.1, 458.1, 459.1

[56] References Cited

U.S. PATENT DOCUMENTS

| | | | |
|---|---|---|---|
| 2,452,522 | 10/1948 | Leverenz | 250/486 |
| 3,049,618 | 8/1962 | Thome | 250/310 |
| 3,449,571 | 6/1969 | Hoerman | 250/461.2 |
| 3,644,044 | 2/1972 | Tolk | 356/314 |
| 3,767,925 | 10/1973 | Foley et al. | 356/314 |
| 3,918,812 | 11/1975 | Holm | 250/461.2 |

OTHER PUBLICATIONS

"Bombardment-Induced Light Emission for the Analysis of Surfaces", Thomas et al., *ACTA Electronica*, 18, 1, 1975, pp. 63–68.

"A Luminescence Spectrophosphorimeter for Measurement of Emissions . . . ", Jameson et al., *Journal of Physics E: Scientific Instruments*, 1976, vol. 9, pp. 208–212.

"Improved Cathodoluminescence Detection System", De Mets, *Journal of Physics E: Scientific Instruments*, 1974, vol. 7, p. 971.

*Primary Examiner*—Alfred E. Smith
*Assistant Examiner*—Jack I. Berman
*Attorney, Agent, or Firm*—Eugen E. Pacher; Richard D. Laumann; Peter V. D. Wilde

[57] ABSTRACT

Emission of characteristic electromagnetic radiation in the infrared, visible, or UV from excited particles, typically ions, molecules, or neutral atoms, desorbed from solid surfaces by an incident beam of low-momentum probe radiation has been observed. Disclosed is a method for characterizing solid surfaces based on the observed effect, with low-momentum probe radiation consisting of electrons or photons. Further disclosed is a method for controlling manufacturing processes that is also based on the observed effect. The latter method can, for instance, be advantageously applied in integrated circuit-, integrated optics-, and magnetic bubble device manufacture. Specific examples of applications of the method are registering of masks, control of a direct-writing processing beam, end-point detection in etching, and control of a processing beam for laser- or electron-beam annealing or ion implantation.

43 Claims, 15 Drawing Figures

METHOD AND APPARATUS FOR SURFACE CHARACTERIZATION AND PROCESS CONTROL UTILIZING RADIATION FROM DESORBED PARTICLES

This is a continuation of application Ser. No. 159,167, filed June 13, 1980.

BACKGROUND OF THE INVENTION

1. Field of the Invention

This invention relates to a method for characterizing solid surfaces by means of characteristic electromagnetic radiation emitted from atoms, ions, and molecules desorbed from the surface by means of incident radiation, and to methods for controlling materials processes by means of this surface characterization method.

2. Description of the Prior Art

The ability to characterize surfaces is a basic and essential requirement in many fields of technology, as well as in research. Many techniques for characterization exist, ranging from the relatively direct one of visual inspection by means of light microscopy to such relatively indirect ones as Auger spectroscopy. See for instance, *Characterization of Solid Surfaces*, P. F. Kane and G. B. Larrabee, editors, Plenum Press, New York and London, 1974, where some twenty surface characterization methods are reviewed.

All such methods have in common that a probe or stimulus is applied to the surface to be studied, and the result of the interaction of the stimulus with the surface is observed. A typical stimulus is radiation, where by "radiation" we mean in this context not just electromagnetic radiation but also corpuscular radiation, such as electrons, ions, atoms, molecules and the like. One of the basic sub-categories of these methods consists of the scattering methods, namely, those that detect and analyze the probe radiation after interaction with the surface. In this category are light microscopy, electron microscopy, X-ray scattering, and the like. Another basic sub-category consists of methods that detect and analyze radiation (other than probe radiation) originating from the surface or from the vicinity of the surface due to the interaction of the surface with the probe radiation. Methods using electron-beam excited X-rays, as for instance, the microbeam technique, X-ray fluorescence analysis, Electron Spectroscopy for Chemical Analysis (ESCA), Auger spectroscopy, and some forms of mass spectrometry are examples of methods belonging in this category. It is this latter category which is of interest in this application, and henceforth, our discussion will be restricted thereto.

A recently developed surface analysis technique utilizes the radiation emitted from excited particles sputtered from a solid surface by means of a low-energy ion or molecular beam. U.S. Pat. No. 3,644,044, issued Feb. 22, 1972, N. H. Tolk, C. W. White, "Method of Analyzing a Solid Surface From Photon Emissions of Sputtered Particles," and U.S. Pat. No. 3,767,925, issued Oct. 23, 1973 to E. B. Foley, Jr., et al, "Apparatus and Method for Determining the Spatial Distribution of Constituents and Contaminants of Solids." See also N. H. Tolk, I. S. E. Tsong, and C. W. White, "In Situ Spectrochemical Analysis of Solid Surfaces by Ion Beam Sputtering," *Analytical Chemistry*, Volume 49, pp. 16A–28A, January 1977. This method, referred to as SCANIIR (Surface Composition by Analysis of Neutral and Ion Impact Radiation) has evolved from recent experiments which showed that electromagnetic radiation, typically in the visible, ultraviolet, or infrared, is produced when beams of low-energy ions or neutral particles impact on a solid surface. Surface constituents can be determined by identification of the characteristic radiation emitted by the desorbed particles. This technique can be essentially nondestructive, since damage to the sample can be minimized by using low incident energies and low current densities. SCANIIR is a very useful analytical laboratory technique, but it is not being used to control or monitor manufacturing processes.

Although a plethora of spectroscopic surface analytic methods exists that rely on relatively low-energy electron probe beams, we will restrict outselves in this discussion of the prior art to those methods that rely on the observation of either an optical response from the sample, or that investigate the properties of particles desorbed from the surface by the probe beam.

The luminescence of surfaces bombarded with fast (100 keV) electrons has been observed some sixty years ago. Recently, it has been noticed that in the case of slow electrons the characteristics of the luminescence, i.e., intensity, polarization, and spectral distribution, are very sensitive to the condition of the surface, thus constituting a potentially useful method of surface characterization. See for instance, O. M. Artamonov and S. M. Samarin, "Radiative Interaction of Slow Electrons with Metal Surfaces," *Radiation Effects*, Volume 40, pp. 201–208 (1979). The luminescence spectra observed are invariably broadband, due to the fact that the radiation arises from excitations in the bulk of the material, albeit very close, i.e., typically within the order of a hundred Angstroms, of the surface. A. Shchurenko et al, "Light Radiation From Sodium Films Bombarded With Slow Electrons," *Solid State Communications*, Volume 33, pp. 141–142 (1980), for instance report optical radiation from Na films bombarded with slow electrons, and attribute the observed broad peak in the spectrum to radiation from surface plasmons. Fluorescence stimulated by low-energy electrons is, of course, not limited to metals. For instance, R. H. Prince et al, "Fluorescence of Ice by Low-Energy Electrons," *The Journal of Chemical Physics*, Volume 64(10), pp. 3978–3984 (1976) report the observation of the emission spectrum of solid $H_2O$ during excitation by 200 eV electrons. The spectrum observed is broadband with some relatively broad peaks. No discrete narrow spectral lines were observed by these authors.

It has been known for some time that bombardment of surfaces with relatively low-energy electrons can lead to the desorption of particles from the surface, referred to in the literature as "Electron-Stimulated Desorption" (ESD). ESD has been observed for species chemisorbed or physisorbed at a solid surface, as well as for surface atoms intrinsic to the sample. A variety of inelastic interactions between the incident electrons and the surface can lead to ESD, although direct momentum exchange, typically the predominant mechanism in sputtering by ions or neutral atoms is not the dominant mechanism in ESD. This is, of course, due to the great disparity in mass between the incident electron and the desorbed particles, which have a mass ratio of at least approximately 1 to 2000. It is easy to show from classical collision theory that under these circumstances the energy transferred to the massive target particle in a direct collision is no more than about $4E_i(m/M)$, where $E_i$ and $m_i$ are the energy and mass of the incident particle, respectively, and M is the mass of the desorbed particle. See for instance, T. E. Madey and J. T. Yates, Jr., "Electron-Stimulated Desorption as a Tool for Studies of Chemisorption: A Review," *The Journal of Vacuum Science and Technology*, Volume 8(4), pp. 525-555 (1971).

ESD can be studied either by methods based on changes in surface properties, or by methods based on the direct detection of desorbed particles. In the latter category are methods based on mass analysis, measurements of ion current and ion kinetic energy, and methods based on detection of secondary electrons. Ibid, also M. Szymonski et al, "Sputtering of Molecules During Low-Energy Electron Bombardment of Alkali Halides," *Surface Science*, Volume 90, pp. 274-279 (1979).

ESD as a technique for surface characterization by means of methods based on the direct detection of desorbed particles has a severe shortcoming. We are referring to the fact that detection and identification of desorbed particles requires either mass spectrometry or relatively complex indirect methods, all of these demanding equipment that is not typically available outside the laboratory, and that in any case is complicated and not conveniently used.

The discussion of the desorption of particles from surfaces has thus far been limited to desorption by means of electron beams. However, it has been recognized that photon beams can have a quite analogous effect, and that, therefore, irradiation of surfaces with appropriately chosen electromagnetic radiation will also lead to stimulated desorption of particles. See for instance, P. D. Townsend, "Photon-Induced Sputtering," *Surface Science*, Volume 90, pp. 256-264 (1979).

SUMMARY OF THE INVENTION

We have discovered the emission of characteristic electromagnetic radiation from particles desorbed from solid surfaces that are exposed to a flux of probe radiation that transfers negligible linear momentum to surface particles. Such probe radiation consists typically of electrons, of energetic electromagnetic radiation of UV or X-ray frequencies, or of high-intensity, low-energy electromagnetic radiation, such as from a laser. Since the emitting particles originate at, or within at the most a few Angstroms of the solid/vacuum interface, the effect is essentially a surface probe only, which distinguishes it from methods that rely on the observation of characteristic X-radiation excited by electron bombardment. These techniques, for instance, electron microbeam techniques, typically probe a layer of the sample of finite thickness, and have, therefore, only limited surface sensitivity. The radiation emitted by the desorbed particles is relatively easily detected, with the most intense observed line corresponding typically to the first resonance line of the emitting particle, i.e., the transition from the first excited state to the ground state. However, this observation is not universally true, and other lines may be quite intense also.

In addition to line radiation from excited neutral atoms or ions, we also observe molecular radiation, which is also emitted from particles desorbed from the surface. As in the prior art, we observe also the emission of continuum radiation from the bulk. By appropriately arranging the optical system required to detect the radiation, it is possible to substantially suppress the unwanted background radiation, i.e., the continuum radiation emitted from the bulk. Such an arrangement substantially increases the signal-to-noise ratio, and thereby permits the observation of weaker lines that otherwise will be buried in the background.

The discovery of the emission of characteristic radiation from desorbed particles can be applied to the characterization of surfaces. It results in a method that is free of the shortcomings of the analogous prior art methods that were reviewed in the previous section. In particular, the inventive method uses an electron beam or electromagnetic radiation as the probe radiation, both of which often serve as the processing radiation in, for instance, LSI (Large Scale Integration) semiconductor device processing. "Processing Radiation" we intend to mean all forms of radiation, electromagnetic as well as corpuscular, in the form of a beam or otherwise, that is used to bring about some intentional change in the condition of an article, other than desorption of surface particles for spectroscopic purposes according to our invention, carried out in a manufacturing context. Thus, our invention makes possible the use of one and the same radiation beam as processing radiation and as probe radiation for characterization or control purposes. Furthermore, using the radiation emitted by the excited particles, typically neutral atoms, ions, or molecules, that have been desorbed from the surface (that is, which are typically noninteracting with other particles) avoids the difficulties associated with the prior art that had observed only radiation from the bulk of materials that were bombarded by electrons. As was mentioned above, optical radiation from the bulk shows only broad features superimposed on a background continuum, the broad features being not specific enough to easily allow identification of the radiating species. In contrast thereto, the inventive method uses the very sharp line radiation from excited desorbed particles, which permits easy identification of the radiating species.

Our discovery can be advantageously applied in numerous ways. For instance, it can be applied as an analytical tool that permits the quantitative study of surfaces, such as composition of clean surfaces, the study of surface layers such as contaminants, deposits, and the kinetics of film growth. It can also serve as an imaging or microscopy method, analogous to scanning Auger microscopy or as a surface sensitive counterpart to high-resolution scanning electron microscopy. The discovery can also be used to obtain the 2-dimensional mapping, as well as, if combined with appropriate surface-removal techniques, the 3-dimensional distribution of one or more constituents of a surface or of the near-surface bulk, respectively.

The disclosed effect can also be applied advantageously in technologically important ways. For instance, in semiconductor manufacture, in particular, in the manufacture of LSI devices, a frequently encountered problem is the necessity to accurately know the position of a beam of radiation with respect to structure on the semiconductor wafer, or to determine the registry of a mask with respect to structure on a wafer. The effect observed by us permits the detection of the characteristic radiation emitted when a probe beam is incident, for instance, on a fiducial mark, or crosses the boundary between two regions of different surface materials or compositions. The observation can often be done in real time and typically with little added instrumentation, thus permitting, for instance, convenient automatic registry and the like. A related application is the automatic control of a direct writing processing beam, or the automatic control of the annealing or melting of selected surface areas by means of pulsed processing beams. In this last application, for instance, a low intensity beam could be used to search for the area to be annealed or melted, and, once the beam is correctly positioned as verified by the observation of the characteristic radiation emitted by appropriately chosen desorbed particles, the beam can be modified to accomplish the desired end. Another application is in the control of etching steps, such as for end-point detection.

As was indicated above, in these applications, as well as in others not enumerated here, it is, in principle, possible to use a single beam of radiation as both processing radiation and probe radiation. Since the detection of the emitted characteristic radiation can be accomplished relatively simply and inexpensively with standard instrumentation, the inventive method for controlling a manufacturing process thus is not subject to the shortcomings of the prior art methods discussed above.

The observed effect is an essentially universal property of solid surfaces. The intensity of emission is a function of the energy of the probe radiation, with a cut-off of intensity at some low incident energy, and saturation of the intensity typically occurring at high incident energy. The details of the energy dependence typically depend on the surface constituents and the nature of the probe radiation, thus the energy dependence of the emitted radiation can serve as a further means of characterizing the desorbed emitting species and the surface from which desorption occurs.

Ion or neutral atom beams can be used in a manner analogous to the above-described use of electron or photon beams, namely, to control processing steps by means of the information derived from the detection and analysis of the electromagnetic radiation emitted from the particles sputtered from the surface by the probe beam. Such an arrangement is most advantageously used when a manufacturing process involves use of ions or neutral atoms as processing radiation, as is now contemplated, for instance, for very-fine-line lithography for semiconductor device processing, or for selected area ion implantation.

DETAILED DESCRIPTION

We have discovered the emission of characteristic electromagnetic radiation from particles desorbed from solid surfaces by a beam of probe radiation that delivers negligible linear momentum to the surface. By "characteristic electromagnetic radiation" we mean atomic line radiation and molecular radiation, as emitted by free particles, namely, free excited atoms, molecules, or ions. The characteristic radiation of concern to us is in the infrared, visible, and ultraviolet part of the electromagnetic spectrum. Thus, this disclosure is not concerned with characteristic X-ray radiation. By "desorbed particles" we mean particles ejected from a surface exposed to a beam of probe radiation, regardless of the exact mechanism leading to the ejection. However, this disclosure is not concerned with particles desorbed from a surface by primarily thermal means, such as, for instance, local melting of a surface. The desorbed particles include particles originating from a film covering the surface, such as, for instance, a film of contaminants, as well as particles intrinsic to the surface of the material studied. However, in all cases the desorbed particles will have originated either directly from the solid vacuum interface that constitutes the physical surface, or within no more than a few Angstroms of that interface. Thus, the discovered effect is inherently surface sensitive, and is substantially unaffected by bulk properties.

Figure 1:
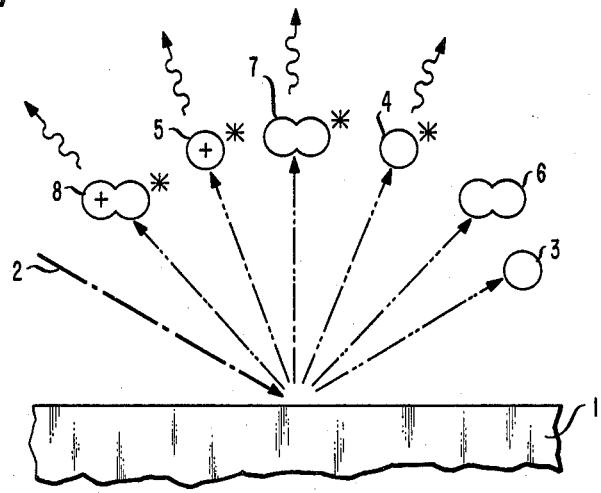
FIG. 1 schematically shows the different categories of particles that can be desorbed from a surface by means of an incident probe beam.

FIG. 1 schematically depicts the kinds of particles that can be desorbed from a surface 1 by means of incident probe beam 2. The probe beam is either an electron or a photon beam, although the kinds of particles desorbed by probe radiation consisting of ion or neutral atom beams is substantially the same. Particle 3 is a desorbed neutral atom, particle 6 a desorbed neutral molecule, particle 4 a desorbed excited atom capable of emitting a photon of characteristic electromagnetic radiation, particle 7 an excited molecule similarly capable of emitting characteristic radiation. Particles 5 and 8 are excited positive ions, both kinds being capable of emitting characteristic radiation. This list of possible desorbed particles is not meant to be exhaustive, and other species of particles may be desorbed under appropriate circumstances.

Figure 2:
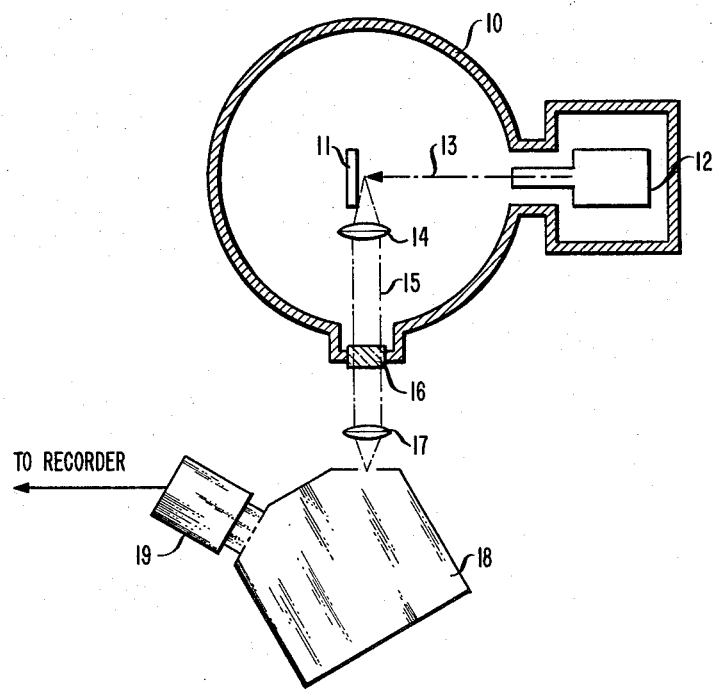
FIG. 2 schematically shows apparatus used to detect radiation from particles desorbed from a solid surface.

FIG. 2 schematically shows apparatus used for observing the emission of characteristic radiation from particles desorbed from a solid surface. Stimulated Desorption (SD) can be achieved by means of a variety of probe beams. This disclosure is concerned with electron beams, high energy photon beams, i.e., beams of photons in the UV- or X-range of the electromagnetic spectrum, as well as lower-energy photon beams of high flux density, typically laser beams. The application is also concerned with ion and neutral atom probe beams, and we intend the term "probe radiation" to include electrons, photons, ions, and neutral atom beams. The term "low momentum probe radiation" will refer to electron and photon beams only. In FIG. 2, vacuum vessel 10 allows maintenance of the sample 11, the source of probe radiation 12, the beam of probe radiation 13, and the collimating lens of the light detection system 14 in a high vacuum. We have carried out measurements in ultrahigh vacuum, of the order of $10^{-9}$ mm Hg, but the vacuum pressure required will depend on the details of the measurement. In particular, the pressure in the chamber should typically be so low that the mean free time of particles desorbed from the surface is longer than the decay time of the appropriate excited species. Although in FIG. 2 the probe beam is shown to be incident normally on the sample surface, this is in no way required, and non-normal incidence may be found advantageous. Radiation 15 emitted from the vicinity of the sample surface is collected by collimating lens 14 and exits from the vacuum chamber through a transparent window 16, and is focused by lens 17 onto the entrance slit of monochromator 18. The monochromator would typically be used in a scanning mode, i.e., it would scan a finite part of the electromagnetic spectrum. However, it may be found advantageous at times to preselect a wavelength of interest and to monitor the change of radiation intensity at this wavelength as a function of time. The monochromator serves to select radiation of a particular wavelength $\lambda$ from the incident radiation and to focus the selected essentially monochromatic radiation onto an exit slit, from where it enters photon detector 19. The output of the photon detector is typically an electrical signal that is proportional to the intensity of radiation of wavelength $\lambda$ in the detected radiation.

Typical apparatus used by us comprises a standard electron gun capable of 15 $\mu$A maximum current and an energy range of 0 to 1 keV. The lens optics consists of UV grade glass and has a magnification factor of unity. The optical instrumentation further comprises a McPherson 0.3 m f-5 monochromator having a grating blazed at 5000 Å, and an EMI 9558QB Photomultiplier having a range from about 1800 to about 8500 Å. The detection scheme used by us is single photon counting. This method is well-known in the art and, therefore, we will not give a detailed account of it. The output of such a detection scheme is typically the photon count per unit time, for instance, one second, as a function of photon wavelength. Apparatus as described here could be used to detect infrared characteristic radiation by substituting a infrared-sensitive phototube. It could be used to detect UV characteristic radiation by arranging for the total optical path to be in vacuum. These requirements are well known in the art.

As shown in FIG. 2, the optical detection system is arranged to permit the detection of light originating from the vicinity of the sample surface and traveling substantially parallel to the surface. This arrangement is advantageous because it greatly reduces the detected background radiation originating from the bulk of the sample. However, such an arrangement is not necessary to practice our invention, and for some purposes a different arrangement of the light detection system may be acceptable.

Figure 3:
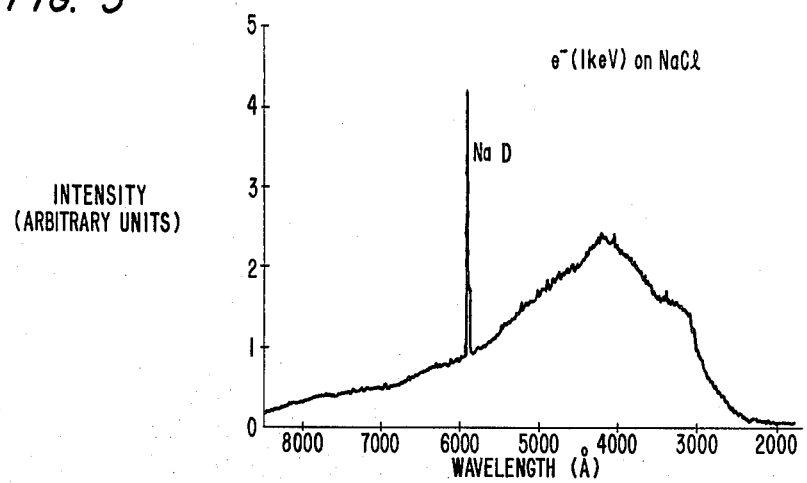
FIG. 3 shows the spectrum observed when an electron beam is incident on a NaCl surface, with the optical detection system arranged to detect also bulk radiation.
Figure 4:
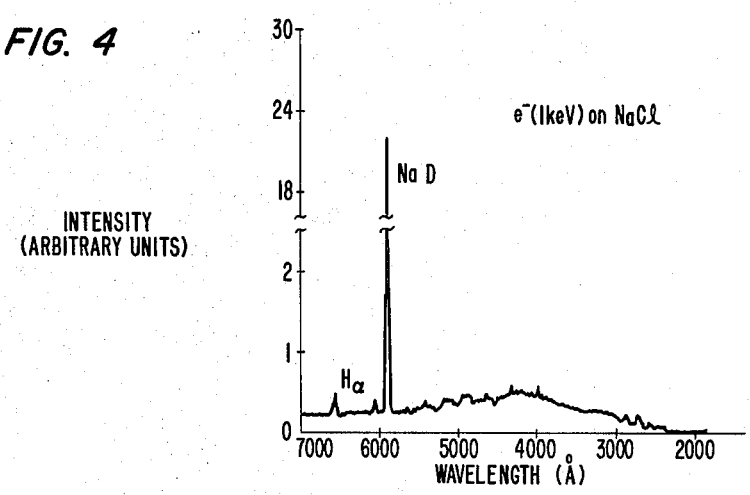
FIG. 4 shows the spectrum observed when electron probe radiation is incident on a NaCl surface, with the optical detection system arranged to detect light traveling substantially parallel to the surface.
Figure 5:
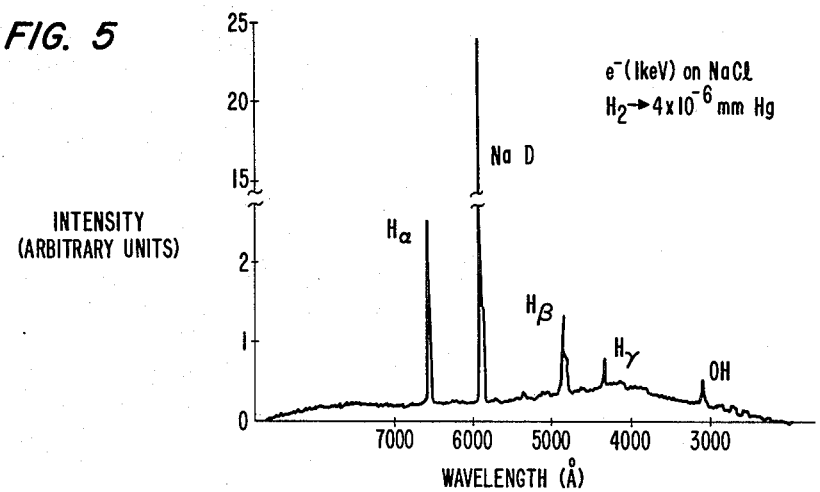
FIG. 5 shows a spectrum observed when electron probe radiation is incident on a NaCl surface that was exposed to a small partial pressure of hydrogen.
Figure 6:
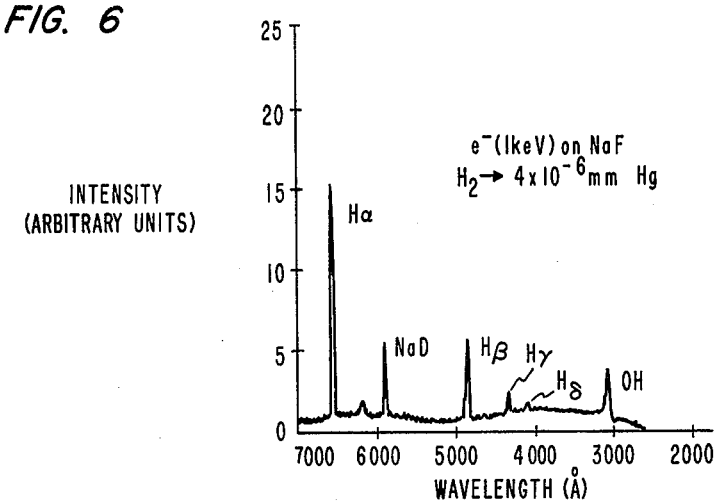
FIG. 6 shows a spectrum observed when electron probe radiation is incident on a NaF surface that was also exposed to a small partial pressure of hydrogen.
Figure 7:
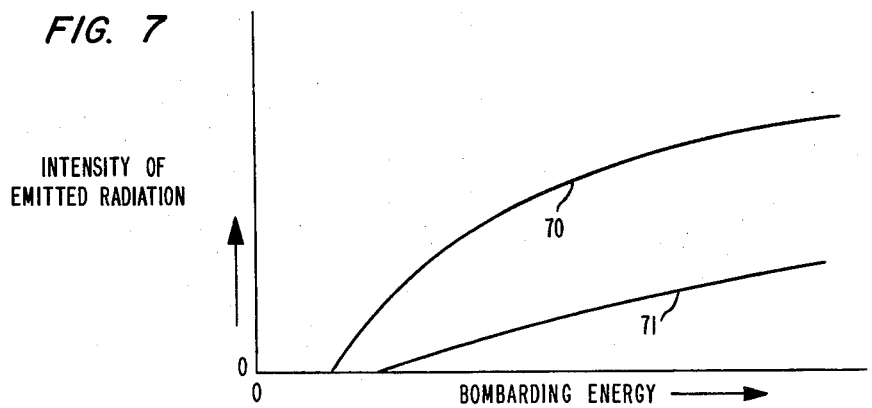
FIG. 7 schematically shows the dependence of the intensity of emitted radiation on the energy of the incident beam, for both characteristic radiation and bulk radiation.
Figure 8:
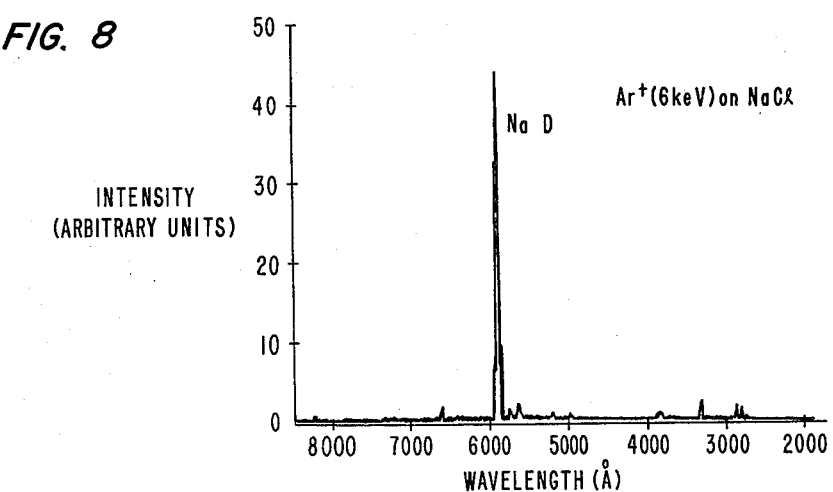
FIG. 8 shows a spectrum observed when $Ar^+$ probe radiation is incident on a NaCl surface.

SD by means of low momentum probe radiation can be used for analyzing solid surfaces, since the emitted characteristic radiation permits the identification of the emitting particles, by well known and standard means, and FIGS. 3 through 6 illustrate this. FIG. 3 shows the spectrum observed when a 1 keV electron beam is incident on a NaCl surface, with the optical detection system making an angle of approximately 45° with the sample normal. A substantial amount of background radiation, originating from the bulk of the sample, is recorded, in addition to a characteristic line at approximately 5890 Å. From standard reference works, such as, for instance, G. P. Harrison, Tables of Wavelengths, MIT Press, Cambridge (1969), this observed line can be identified as the well-known Na D line, emitted by the Na atoms desorbed by the probe beam from the surface. FIG. 4 shows a spectrum obtained under the same conditions as the spectrum shown in FIG. 3, with the exception of a changed arrangement of the optical detection system. In particular, the spectrum shown in FIG. 4 was obtained with the detection system "parallel" to the sample surface, i.e., the detection system was arranged to collect radiation originating from the vicinity of the sample surface and travelling in a direction substantially parallel to that surface. The improvement in the signal-to-noise ratio resulting from this arrangement is immediately obvious from the Figure. In addition to the line radiation at 5890 Å there is now resolved a further line at approximately 6563 Å, which can be identified to be the $H_\alpha$ line. The detection of a hydrogen line, of course, indicates the presence of hydrogen atoms or molecules adsorbed on the surface. FIGS. 5, 6 and 8 also show spectra obtained with the optical detection system arranged "parallel" with the sample surface. The spectrum presented in FIG. 5 was obtained from a sample of NaCl maintained in a hydrogen atmosphere of $4.10^{-6}$ mm Hg during bombardment. In addition to the previously observed Na D line, the spectrum shows a characteristic line at approximately 6563 Å of substantially greater intensity than the line of equal wavelength shown in FIG. 4. In addition, there are lines at approximately 4861 A and 4371 A, which can be identified as the $H_\beta$ and $H_\gamma$ lines, respectively. In addition, the spectrum shows molecular radiation at approximately 3064 Å, which can be identified as the well-known 3064 Å-system of OH. FIG. 6 shows a spectrum obtained when an electron beam is incident on a NaF surface that was similarly maintained in a hydrogen atmosphere of $4.10^{-6}$ mm Hg. The instant spectrum shows the same lines as the spectrum shown in FIG. 5. In addition, it shows an additional weak line which can be identified to be the $H_\delta$ line. But comparing the spectrum of FIG. 6 to the spectrum of FIG. 5 reveals significant differences in the intensities of the observed lines for the two cases. This indicates the sensitivity of stimulated desorption to the details of atomic bonding and the like. Relative intensities of the observed characteristic radiation thus provide further means of characterizing surfaces. FIG. 7 schematically shows the intensity of emitted radiation as a function of energy of the incident low momentum probe beam. Curve 70 shows the variation of characteristic radiation, for instance, the Na D line, and curve 71 shows the variation in the intensity of radiation from the bulk, measured at a wavelength close to the wavelength of the characteristic radiation of curve 70. It will be noted that the ratio between the two intensities is not constant with energy, and therefore, the line/background ratio at a particular wavelength can be improved by appropriate selection of the energy of the probe beam. Furthermore, the cut-off energy of both the characteristic radiation and the bulk radiation is typically a function of atomic species involved, and determination of these cut-off frequencies can thus provide further means for characterizing a solid surface.

Our discovery thus provides a method for determining the identities and also the relative concentration of constituents of a solid sample, since the wavelength at which the spectral lines or peaks of the emitted characteristic radiation occur permit identification of the emitting species, and therefore, of the surface constituents, and since the intensities of the emitted lines are a function of the relative concentrations of the constituents. As has been stated previously, the method involves exposing the surface area of interest to a beam of low momentum probe radiation of appropriate energy and intensity. But since a variety of factors, including efficiency of desorption from the sample surface, sensitivity of the detection apparatus, susceptibility of the sample to radiation damage, and thermal properties of the sample, have to be considered in determining the appropriate beam parameters, no general rules for their determination can be given. For DC electron beams, useful currents are in the $\mu A$ range, with energies in the range from approximately 100 eV to tens of keV. Of course, these approximate bounds are not to be interpreted as constituting absolute limits, since higher or lower energies or currents may be appropriate under some circumstances.

If the probe beam is a photon beam, then one can distinguish two situations, namely, the case of high-energy photons and that of low-energy photons. By high-energy photons, we mean those in the UV- or X-region of the electromagnetic spectrum, i.e., photons of sufficient energy to cause the desorption of a particle from the surface by means of single photon excitation. By low-energy photons on the other hand, we mean photons in the visible and near infrared part of the spectrum that are not able to desorb particles from typical surfaces by means of single photon excitations, but can do so only by means of multi-photon excitations. For this mechanism to be effective, a high density of photons is required, which typically makes necessary the use of a laser as the source of the photon beam. However, other high intensity sources may be found to provide sufficient light flux for some applications. A convenient dividing line between the low-energy and high-energy regions is in the near UV, approximately 2000 A, although the actual value depends on the nature of the system studied.

The inventive method can be practiced in a number of ways. For instance, the probe beam can be incident on a relatively large part of the surface studied, resulting in information on the average composition of the surface. On the other hand, the probe radiation can be focused onto a relatively small surface area, thereby obtaining information as to the surface composition of a particular small surface area. In an advantageous extension of this last mentioned approach, a focused beam of probe radiation can be scanned over a surface area, resulting in a two-dimensional mapping of the distribution of surface constituents. In combination with appropriate surface removal methods, such as, for instance, means for plasma or ion beam etching, the inventive method can give information on the distribution of constituents in the near-surface bulk of the sample. To accomplish this, one can either rely on the inherent desorptive activity of the probe beam to remove surface material, measuring the intensity of appropriate spectral peaks as a function of time, or one can employ a stepwise approach, i.e., measuring the surface concentration of one or more constituents, removing a layer of material of known thickness by the means indicated above, followed by another determination of the surface concentrations. These steps, of course, can be repeated. If this approach is combined with means for scanning the probe beam, then in this fashion, a three-dimensional mapping of concentration of constituents of the sample can be obtained. All of the approaches indicated, of course, can be practiced either with continuous probe beams or with pulsed probe beams.

Although the data shown in FIGS. 3-6 involve a very small number of different surface constituents, the novel effect, i.e., the emission of characteristic radiation from particles desorbed by means of low-momentum probe radiation beams, is substantially universal. Therefore, the inventive method of surface characterization has also very broad applicability. In Table I, we are giving examples of elements together with a wavelength at which strong characteristic radiation from each listed element can be observed.

TABLE I

| Particle | Wavelength (A) | Character |
|---|---|---|
| Al | 3962 | line |
| Cr | 4254 | " |
| Ni | 3524 | " |
| Ga | 4172 | " |
| In | 4511 | " |
| Li | 6707 | " |
| Nd | 4304 | " |
| Y | 3601 | " |
| Pt | 2695 | " |
| Ir | 2662 | " |
| Si | 2882 | " |
| Ge | 3039 | " |
| C | 1302 | " |
| H | 6563 | " |
| OH | 3063 | molecular |
| CH | 4300 | " |

The emission of characteristic radiation from particles desorbed from solid surfaces by means of a beam of probe radiation forms also the basis of an advantageous method for controlling or monitoring manufacturing processes. In a generalized form of the method, a beam of probe radiation is caused to be incident on a surface of a solid article, resulting in the desorption of particles from that surface, and the emission of characteristic radiation from excited desorbed particles. This radiation is detected in a manner similar to that described above. The signal derived from the detector contains information as to the presence or absence of a certain element in the surface, and the concentration of various constituents present in the surface. This information can be used to control or monitor, either automatically or manually, a processing step. The method is applicable in a multitude of manufacturing processes, and we give below examples of such applications. However, the method is most advantageously used in conjunction with manufacturing processes and apparatus involving processing radiation, such as electron, photon, ion, or neutral atom beams, to accomplish certain processing steps. The reason for this is, inter alia, that processing with such radiation is typically carried out in vacuum, and in apparatus that is typically easily adaptable to the inventive method. However, no restriction to such situations is intended, and in fact, situations exist where the inventive method can be advantageously applied in the absence of a beam of processing radiation, such as, for instance, for determining the end-point of an etching processing step in IC manufacture.

A particularly advantageous situation exists when the beam of processing radiation and the beam of probe radiation can be of the same kind, perhaps differing in intensity, energy, or beam diameter. Examples of such cases will be given below. It is to be noted that for these applications both process radiation and probe radiation may consist of ion beams or neutral atom beams, in addition to the electron or photon beams previously discussed. The characteristic spectra observed when such heavy particle beams are used for desorbing particles from a solid surface are quite similar to those observed when low momentum beams are used, and FIG. 8 shows an example of such a spectrum. It was obtained when a 6 keV Ar+ beam was incident on a NaCl surface, and shows, inter alia, a very intense Na D line.

Figure 9:
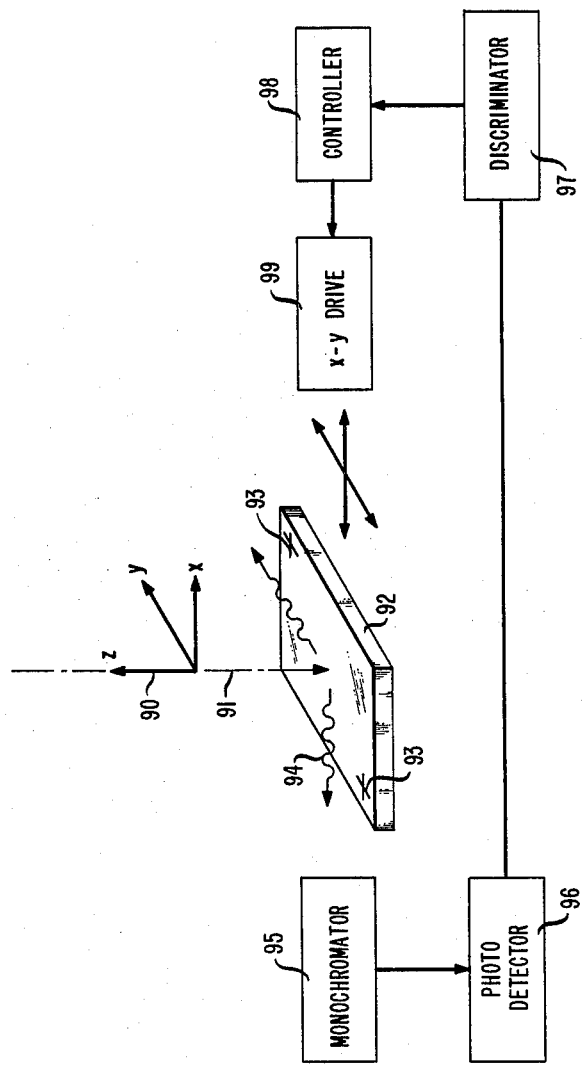
FIG. 9 schematically shows apparatus for controlling a manufacturing step by means of the inventive method.

FIG. 9 schematically shows apparatus used in practicing the inventive method as a means of process control. Coordinate system 90 is included in the Figure to make the discussion more definite. Probe beam 91, traveling in the negative z-direction, is incident on a surface of article 92. Emitted characteristic radiation 94 is collected, typically by an optical system, and enters monochromator 95, which serves to isolate a very narrow region of the spectrum from the emitted radiation, and the intensity of the light in this narrow spectral region is detected by photodetector 96. Discriminator 97 functions to distinguish between photodetector outputs below and above a predetermined threshold. For instance, if the output is above such threshold, the discriminator activates controller 98, which in turn, switches on some actuating device, such as, for instance, X-Y drive 99, which translates the article in the X-Y plane in response to the emitted radiation. FIG. 9, of course, is only meant to indicate a possible scheme of control, and those skilled in the art can easily adapt the shown scheme to particular requirements, or design different schemes.

We will now discuss some typical manufacturing processes in which the inventive method could be advantageously applied. In the manufacture of integrated circuits, integrated optical devices, magnetic bubble devices, to name only a few, it is typically necessary to align a processing mask with respect to structure on a surface of an article, for instance, a semiconductor wafer. Typically, the surface would be covered with a processing layer, such as, for instance, a photoresist, and only predetermined areas are to be exposed to processing radiation. This selective exposure is accomplished by interposing a mask between processing layer and the source of processing radiation. Such a mask consists of regions transparent to the processing radiation, as well as of regions nontransparent thereto. In order to achieve registry between mask and underlying article, typically fiducial marks on the mask are brought into coincidence with fiducial marks on the article. In order to utilize the inventive method in this application, the fiducial marks on the article typically contain a constituent element that is not present in the surface of the article. Thus, if the probe beam is incident upon the article's fiducial mark then characteristic radiation will be emitted that is not present in the spectrum originating from other parts of the surface. This obviously allows determination of registry.

Figure 10:
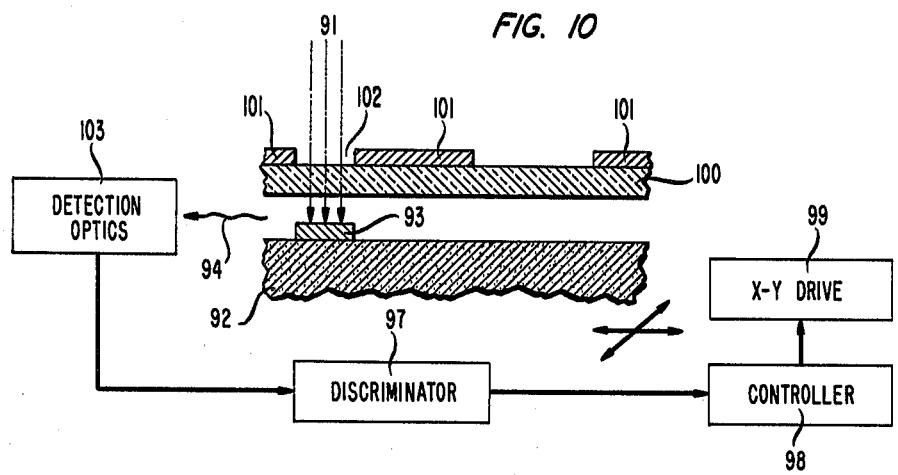
FIG. 10 schematically illustrates an exemplary application of the inventive method, namely registering a processing mask with respect to a fiducial mark on an article surface.

This application is schematically illustrated in FIG. 10, where, as is the case for all the figures herein, corresponding parts in different figures are designated by the same numeral. Probe beam 91 is incident on fiducial mark 93 on the surface of article 92, after passing through transparent (to the probe radiation) mask substrate 100, carrying opaque (to the probe radiation) layer 101. Window 102 in 101 is brought into alignment with the fiducial mark by directing beam 91 through the window and observing emitted characteristic radiation 94 by means of, e.g., detection optics 103 (comprising, for instance, focussing means, a monochromator, and a detector), by monitoring the detected light intensity at a predetermined wavelength $\lambda_o$, by means of, e.g., discriminator 97, and by, e.g., translating the article with respect to window 102 by means of X—Y drive 99, activated by controller 98, with 98 being responsive to the state of 97.

Figure 12:
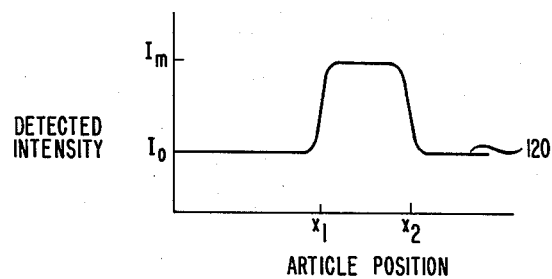
FIG. 12 is a schematic plot of detected light intensity as a function of probe beam position, as is observed, for instance, when scanning the probe beam across a fiducial mark on an article surface.

Typically, the monochromator would be adjusted such as to allow monitoring of radiation at a predetermined wavelength $\lambda_o$. If the intensity of the radiation at $\lambda_o$ is $I_o$ when the probe beam is not incident upon a fiducial mark on the article, and the intensity is substantially different from $I_o$ when the probe beam is incident on the fiducial mark, then the occurrence of intensity $\neq I_o$ indicates existence of alignment between beam and fiducial mark. This is illustrated in FIG. 12, in which curve 120 schematically depicts the detected light intensity at $\lambda_o$ when, e.g., a sample surface is scanned under a probe beam held fixed in space. Intensity $I_o$ is observed when the beam is incident on the sample surface, and $I_m$ when the beam is fully incident on a chemically different surface feature, e.g., a fiducial mark "extending" from article coordinate $x_1$ to $x_2$.

After alignment has been established, the processing layer is exposed to processing radiation through the transparent regions of the mask, resulting in a transformation in the exposed regions that results in a difference in interaction rate with some appropriate reactive medium, such as a wet etch or plasma. This difference in reaction rate leads to removal of only the exposed or only the unexposed portion of the processing layer when exposed to the reactive medium, depending on the details of the system. Following completion of the selective removal of the processing layer, i.e., after the underlying substrate regions have become bared, a variety of processing steps can be carried out. These include etching, ion implantation, diffusion of dopants, modification of the physical state of the substrate regions, such as recrystallization or annealing.

Procedures of the kind described are being carried out on many substrate materials. A very partial listing includes Si, Ge, $SiO_2$, metal silizides, GaAs, AlGaAs and other ternary and quaternary semiconductors including Ga and As, InP, $LiNbO_3$, many different kinds of garnets used, or potentially useful, in magnetic bubble devices or integrated optics, hydrogenated silicon used in solar cells, Al, Cr, Au, Ni, Pt, and silicon nitride. Many different kinds of photoresists and the like are known that can be used as processing layers of the kind described above, including both organic and inorganic compounds. We will not describe these further.

The inventive method can also be advantageously applied to the control of direct writing beam exposure systems, as are currently used in mask making, as well as are being developed for direct writing processing of large scale integrated circuits and the like. See, for instance, U.S. Pat. No. 3,900,737, issued Aug. 19, 1975 to R. J. Collier et al, entitled "Electron Beam Exposure System." In this latter application the selectivity of exposure of regions of processing layer is achieved not through masking but through control of a very fine beam of processing radiation. Processing steps subsequent to the exposure step are typically the same in this approach than they are in the "mask" approach as described above.

Figure 11:
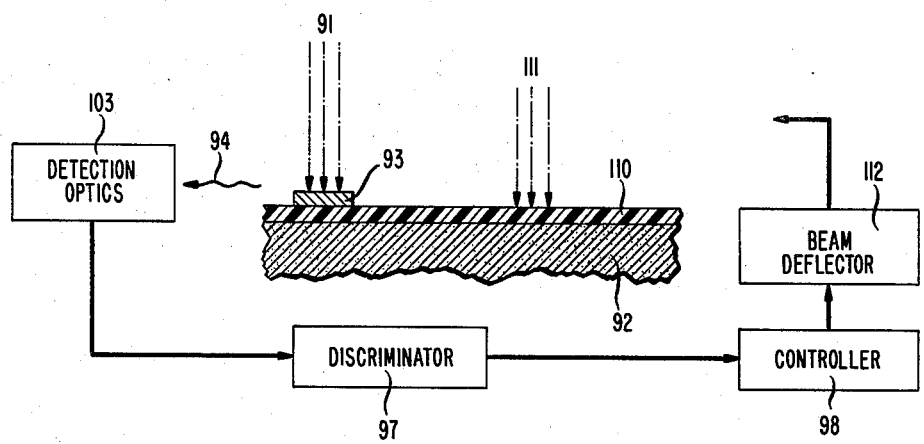
FIG. 11 schematically shows another exemplary application, namely exposing a part of a processing layer on a sample surface to processing radiation, with the coordinates of the exposed part determined with respect to a fiducial mark.

Exposure of selected regions of a processing layer to a direct writing processing beam is schematically illustrated in FIG. 11, in which processing layer 110 carries fiducial mark 93. The spatial relationship between 93 and the region of 110 exposed to processing beam 111 is changed by means of, e.g., beam deflector 112, responsive to radiation 94, resulting in patterned exposure of layer 110.

As disclosed in the above-identified patent, the exposure is accomplished by a step-and-repeat procedure, which requires very high precision in the electronic and mechanical stability of the apparatus. These requirements are less severe if it is possible to repeatedly check actual beam position on the article surface against expected beam position. This can be easily achieved by putting fiducial marks of the kind referred to in the previously described application onto the surface of the article being processed. The coordinate system used to describe the surface structure of the article can be located with respect to the fiducial marks, which represent fixed points with known coordinates. This permits easy verification of the actual position of the probe beam incident upon the surface, and allows correction of the beam position with respect to the article coordinate system. An advantageous way of implementing the inventive method for the present purpose is to use the beam of process radiation to serve also as probe radiation, and by comparing the beam coordinates when the beam is incident upon a fiducial mark with predetermined coordinates stored in a storage device, such as, for instance, a computer. Beams useful in this application are, inter alia, electron beams, ion beams or high-energy photon beams, such as, UV or X-radiation beams. In practice, one typically incorporates means for discriminating between levels of intensity of radiation at predetermined wavelengths into the apparatus, in a manner similar to that described in conjunction with the mask registration application.

Figure 13:
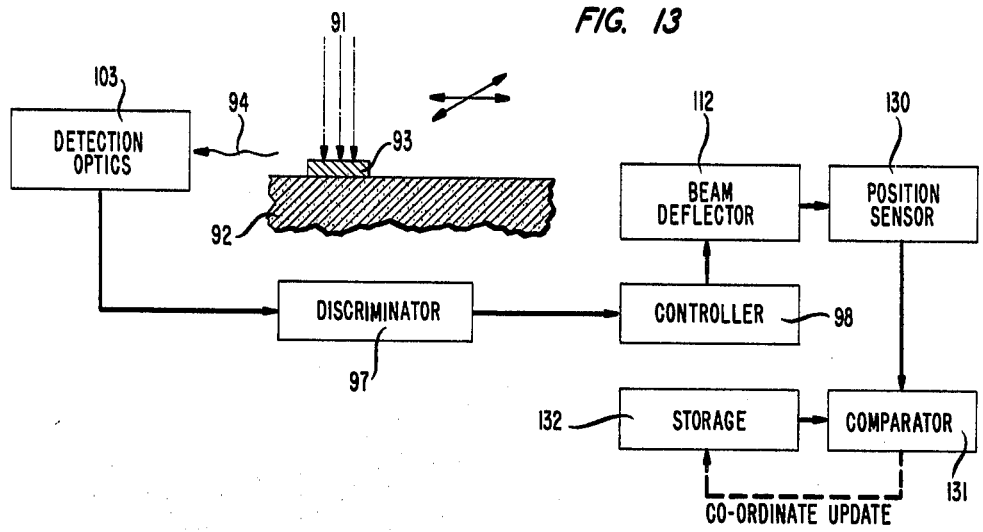
FIG. 13 schematically shows a further exemplary application of the inventive method, namely updating or correcting stored coordinate values of a fiducial mark on an article surface.

FIG. 13 schematically illustrates use of the invention for updating or correcting coordinate information in a direct writing exposure system. Probe beam 91, which can, for instance, be a reduced intensity electron processing beam, is caused to be incident on 93 by means of beam deflector 112, controlled by controller 98, responsive to radiation 94. The state of 112 upon coincidence of 91 and 93 is sensed by position sensor 130, and the state information transmitted to comparator 131, where it is compared to the corresponding information in storage means 132, e.g., in a computer memory. If appropriate, the information in 130 is then updated or corrected.

The inventive method can also advantageously be applied to the solution of the problem of determining the end point of an etching step. As described above, in integrated circuit manufacture as well as in many other manufacturing fields, it is necessary to remove part of a process layer by means of contacting the parts to be removed with a reactive medium. In particular, we are considering the problem of removing a process layer of initial thickness t deposited on a substrate, without removing substantial amounts of substrate material. The control of the removal step can be achieved by detecting the instant when the underlying substrate has become bared to the reactive medium. The inventive method is particularly well adapted to this application. A beam of probe radiation is caused to be incident on a region of the article from which the processing layer is being removed, typically a test region. The beam causes stimulated desorption of particles from the test region. The detection system is to be adjusted to detect characteristic radiation from a constituent that is present in the substrate but absent from the processing layer, or vice versa. As soon as the detection system detects the presence of radiation at this wavelength of sufficient intensity, or the decrease of intensity below a predetermined background level, as the case may be, the etching is to be terminated. This method of end point detection can be practiced advantageously with, inter alia, plasma etching, as well as ion etching.

Figure 14:
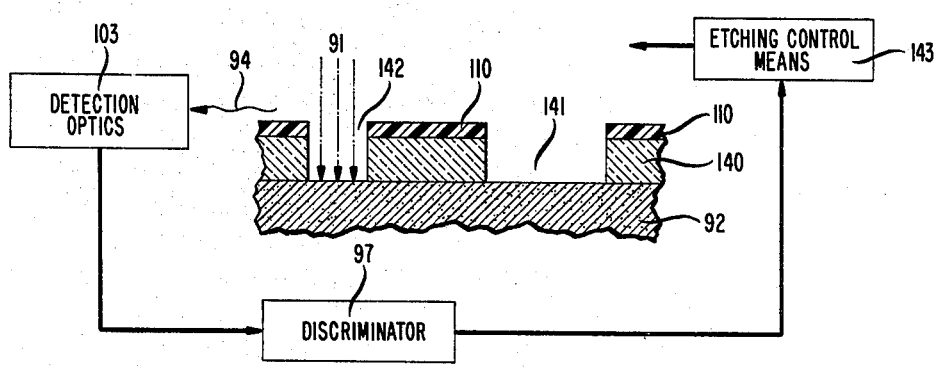
FIG. 14 is a schematic illustration of another exemplary application, etching endpoint detection.

This is schematically illustrated in FIG. 14, showing a patterned processing layer 110, e.g., a resist layer, on layer 140, e.g., a $SiO_2$ layer. The pattern of 110 is being reproduced in 140, for instance, a window 141 is being etched through 140 to the underlying region of article 92, e.g., a Si wafer. Layer 110 contains a test region 142, and probe beam 91, incident on the surface in the test region, causes desorption of surface particles and radiation emission therefrom. Upon etching, by contact with a medium not shown, e.g., an ion beam, through layer 140 in the test region, the nature of emitted radiation changes. This change is detected by means described above, and produces a controller output that changes the state of etching control means 143, e.g., switches off the ion beam.

A further advantageous application of the inventive method is in the control of selected area surface treatment by means of process radiation, such as, for instance, annealing, melting, or ion implantation of predetermined surface areas of an article. Such treatments involve changing not only the state of the surface but also that of part of the article underlying the exposed surface region. It is assumed that the surface region to be processed differs from adjacent areas not to be processed in at least one constituent, such that the presence or absence of some characteristic radiation in the spectrum indicates whether or not the probe beam is properly incident upon the selected region. After proper alignment of the probe beam has been achieved, a processing beam could be directed to the same area as marked by the incident probe beam or, more advantageously, the intensity or energy or other suitable beam parameter of the probe beam could be changed to transform the probe beam into the processing beam. Beams useful in this application include electron beams, high-intensity low-energy photon beams, as from a laser, ion and neutral atoms beams.

Figure 15:
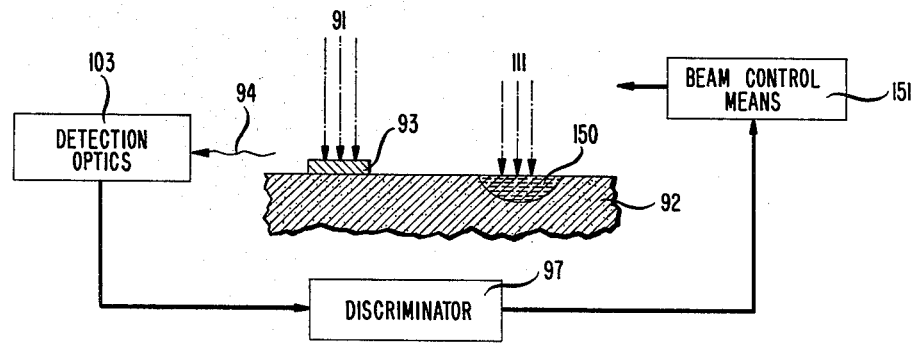
FIG. 15 is a further schematic illustration of an exemplary application, exposing a part of a sample surface to processing radiation, with the coordinates of the exposed part determined with respect to a fiducial mark.

Selected area treatment according to the invention is schematically illustrated in FIG. 15, in which processing beam 111 is responsive, through beam control means 151, to position information obtained by means of probe beam 91 and fiducial mark 93, in a manner previously described. The processing beam is incident on a part of the surface of article 92, and causes a change in region 150, e.g., melting or annealing, or a change in composition through ion implantation.

All of the enumerated applications are easily automated, and thus the inventive method leads to substantial improvement in such important manufacturing areas as integrated circuit-, integrated optics-, and magnetic bubble device manufacture. However, the application of the inventive method is not restricted to these manufacturing areas. The applications enumerated above are to be considered only exemplary, and the scope of our invention is only limited by the claims.

We claim:
1. Method for analyzing a solid surface comprising
   (a) exposing at least part of the surface to a beam of probe radiation of intensity and energy such that the exposed surface area remains solid;
   (b) detecting responsive characteristic electromagnetic radiation in the infrared, visible, or UV part of the spectrum emitted by excited particles desorbed from the surface;
   characterized in that
   (c) the probe radiation consists of low-momentum radiation, "low-momentum radiation" being radiation that transfers negligible linear momentum to particles in the surface.
2. Method of claim 1, wherein the probe radiation consists of electrons.
3. Method of claim 1, wherein the probe radiation consists of photons.
4. Method for analyzing a solid sample comprising at least one chemical species and having a surface, the method comprising
   (a) exposing at least part of the surface to a beam of probe radiation, of intensity and energy such that the exposed surface area remains solid, to desorb particles from the surface and produce characteristic photon emissions from at least a portion of the desorbed particles;
   (b) detecting at least a portion of the photon emissions in the infrared, visible, or ultraviolet part of the electromagnetic spectrum so as to obtain electrical signals, and
   (c) processing the signals so as to obtain at least a portion of a characteristic spectrum, the wavelengths at which spectral peaks occur indicating the identity of the species, and the intensities of the peaks indicating the relative concentrations of the species,
   characterized in that
   (d) the probe radiation consists of low-momentum radiation, "low-momentum radiation" being radiation that transfers negligible linear momentum to particles in the surface.
5. Method of claim 2, wherein the probe radiation consists of electrons.
6. Method of claim 4, wherein the probe radiation consists of photons.
7. Method of claim 6 wherein the photon beam comprises photons of energy sufficient to cause desorption of the chemical species by means of a single-photon process.
8. Method of claim 6 wherein the photon beam comprises a high-intensity flux of photons of energy insufficient to cause desorption of the chemical species by means of a single-photon process, the flux and the energy adapted to result in desorption of the species by means of a multiphoton process.
9. Method of claim 4 wherein the beam of probe radiation is substantially brought to a focus at the surface.
10. Method of claim 9, wherein the beam of probe radiation is caused to scan over at least part of the surface.
11. Method of claim 10, wherein the signals obtained are processed to yield an output proportional to the intensity of at least one spectral peak as a function of position, thereby mapping the relative concentration of at least one chemical species in the part of the surface scanned.
12. Method of claim 9, wherein the signals obtained are processed to yield an output proportional to the intensity of at least one spectral peak as a function of time, thereby indicating the relative concentration of at least one chemical species in the solid sample as a function of depth in the sample.
13. Method of claim 12, wherein the beam of probe radiation is caused to scan over at least part of the surface, thereby mapping the three-dimensional relative concentration of at least one chemical species in the solid sample.
14. Method of claim 4, wherein at least a portion of the photons traveling in a direction substantially parallel to the surface are detected.
15. Apparatus for analyzing a solid sample comprising at least one chemical species and having a surface, the apparatus comprising
   (a) means for producing a beam of probe radiation,
   (b) means for exposing at least part of the surface to the beam of probe radiation to desorb particles from the surface and produce characteristic photon emissions from at least a portion of the desorbed particles,
   (c) means for detecting at least a portion of the photon emissions in the infrared, visible, or ultraviolet part of the electromagnetic spectrum so as to obtain electrical signals, and
   (d) means for processing the signals so as to obtain at least a portion of a characteristic spectrum, the wavelengths at which spectral peaks occur indicating the identity of the chemical species, and the relative intensities of the peaks indicating the relative concentrations of the species,
   CHARACTERIZED IN THAT
   (e) the means for producing a beam of probe radiation produce a beam of low-momentum radiation of intensity and energy such that the exposed surface area remains solid, "low-momentum radiation" being radiation that transfers negligible linear momentum to particles in the surface.
16. Apparatus of claim 15, wherein the beam of low-momentum probe radiation is an electron beam.
17. Apparatus of claim 15, wherein the beam of probe radiation is a photon beam.
18. Apparatus of claim 15, wherein the means for detecting photon emissions are adapted to detecting photons traveling substantially parallel to the surface.
19. Method for controlling a manufacturing process comprising a multiplicity of manufacturing steps, the method comprising
   (a) exposing at least a part of a surface of a solid article to a beam of probe radiation of intensity and energy such that the exposed surface area remains solid,

(b) detecting responsive characteristic electromagnetic radiation in the infrared, visible, or UV part of the spectrum emitted by excited particles desorbed from the surface,

CHARACTERIZED IN THAT (c) the beam of probe radiation consists of low-momentum radiation, "low-momentum radiation" being radiation that transfers negligible linear momentum to particles in the surface, and

FURTHER CHARACTERIZED BY (d) adjusting at least one of the manufacturing steps in response to the detected characteristic electromagnetic radiation.

20. Method according to claim 19, wherein the beam of probe radiation consists of electrons.

21. Method according to claim 19, wherein the beam of probe radiation consists of photons.

22. Method according to claim 19 wherein the responsively adjusted manufacturing step comprises registering a processing mask with regard to at least one fiducial mark on the surface of the article.

23. Method according to claim 19, wherein the responsively adjusted manufacturing step comprises exposing at least a part of the surface of the article to a beam of process radiation.

24. Method according to claim 23, wherein the beam of process radiation serves also as the beam of probe radiation.

25. Method according to claim 24, wherein the coordinates of the surface area to be exposed are determined with regard to the coordinates of at least one fiducial mark on the surface of the article.

26. Method according to claim 22, wherein (a) the surface constituents yield responsive radiation of intensity $I_o$ at wavelength $\lambda_o$ when exposed to a beam of probe radiation, and (b) the fiducial mark comprises a constituent yielding responsive characteristic radiation of intensity substantially different from $I_o$ at $\lambda_o$ when exposed to substantially the same beam as in (a).

27. Method according to claim 25, wherein (a) the surface constituents yield responsive radiation of intensity $I_c$ at wavelength $\lambda_o$ when exposed to a beam of probe radiation, and (b) the fiducial mark comprises a constituent yielding responsive characteristic radiation of intensity substantially different from $I_o$ at $\lambda_o$ when exposed to substantially the same beam as in (a).

28. Method according to claim 15, wherein the responsively adjusted manufacturing step comprises (a) comparing the coordinates of at least one fiducial mark with preassigned coordinates stored in a storage device, and (b) adjusting the stored coordinates in response to the result of the comparison.

29. Method according to claim 19 wherein the responsively adjusted manufacturing step comprises an etching step, the etching step being terminated in response to the characteristic radiation detected.

30. Method according to claim 29, wherein the etching step comprises plasma etching.

31. Method according to claim 29, wherein the etching step comprises ion or neutral atom etching.

32. Method according to claim 29, wherein (a) the constituents of at least a part of the surface layer of the article yield responsive radiation of intensity $I_o$ at a wavelength $\lambda_o$ when exposed to a beam of probe radiation, and (b) the constituents of at least a part of the article substrate underlying the part of the surface layer yield responsive radiation of intensity substantially differing from $I_o$ at $\lambda_o$ when exposed to substantially the same beam as in (a).

33. Method according to claim 19, wherein the responsively adjusted manufacturing step comprises exposing at least part of the surface to a beam of processing radiation adapted to changing the state of the exposed surface region and of at least part of the volume of the article underlying the exposed surface region.

34. Method according to claim 28, wherein the beam of processing radiation serves also as the beam of probe radiation.

35. Method according to claim 33, wherein the changing of the state comprises melting.

36. Method according to claim 33, wherein the changing of the state comprises implanting ions or neutral atoms into the article.

37. Method for manufacturing an article having a solid surface, the method comprising a multiplicity of manufacturing steps, with the article comprising during at least one manufacturing step a processing layer disposed on a substrate layer, the method comprising (a) exposing selected areas of the processing layer to processing radiation adapted to cause a difference in reaction rate between exposed and unexposed areas of the processing layer with a reactive medium, and (b) exposing the processing layer to the reactive medium for a time sufficient to remove the processing layer disposed over selected areas of the substrate layer, characterized in that the method further comprises (c) exposing at least a part of the surface of the article to a beam of low-momentum probe radiation, of intensity and energy such that the exposed surface area remains solid, "low-momentum radiation" being radiation that transfers negligible linear momentum to particles in the surface, (d) detecting responsive characteristic electromagnetic radiation in the infrared, visible, or UV part of the spectrum emitted by excited particles desorbed from the surface, and (e) adjusting at least one manufacturing step in response to the detected characteristic electromagnetic radiation.

38. Method of claim 37, wherein the probe radiation consists of electrons.

39. Method of claim 37, wherein the probe radiation consists of photons.

40. Method according to claim 37, wherein the manufacturing step adjusted in response to the detected characteristic electromagnetic radiation comprises registering a processing mask with regard to at least one fiducial mark on the surface of the article.

41. Method according to claim 37, wherein the manufacturing step adjusted in response to the detected characteristic electromagnetic radiation comprises determining the location of the selected areas of the processing layer to be exposed to processing radiation with respect to at least one fiducial mark on the surface of the article.

42. Method according to claim 37, wherein the manufacturing step adjusted in response to the detected characteristic electromagnetic radiation comprises determining the moment of time when the processing layer disposed over selected areas of the substrate has been removed due to exposure of the processing layer to the reactive medium.

43. Method according to claim 37, wherein the manufacturing step adjusted in response to the detected characteristic electromagnetic radiation comprises exposing at least a part of the selected areas of the substrate layer to a beam of processing radiation adapted to changing the state of the exposed surface region and of at least part of the volume of the article underlying the exposed surface region.

* * * * *